(12) United States Patent
Tanio et al.

(10) Patent No.: US 7,530,973 B2
(45) Date of Patent: May 12, 2009

(54) SANITARY NAPKIN HAVING THREE-DIMENSIONAL STRUCTURE IN INTERGLUTEAL CLEFT-FACING REGION

(75) Inventors: Toshiyuki Tanio, Kagawa (JP); Wataru Yoshimasa, Kagawa (JP); Kenichiro Kuroda, Kagawa (JP); Shinobu Fujikawa, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 321 days.

(21) Appl. No.: 11/124,562

(22) Filed: May 5, 2005

(65) Prior Publication Data
US 2005/0267435 A1 Dec. 1, 2005

(30) Foreign Application Priority Data
May 27, 2004 (JP) ............................. 2004-156959

(51) Int. Cl.
*A61F 13/536* (2006.01)

(52) U.S. Cl. .............. 604/385.27; 604/380; 604/385.31

(58) Field of Classification Search ......... 604/379–380, 604/385.17, 385.27, 385.04, 385.31
See application file for complete search history.

(56) References Cited

U.S. PATENT DOCUMENTS

| 2,331,355 | A | * | 10/1943 | Strongson | 604/365 |
| RE24,385 | E | * | 10/1957 | Flanders | 604/364 |
| 3,247,846 | A | * | 4/1966 | Fansler | 602/79 |
| 4,484,919 | A | * | 11/1984 | Sohn et al. | 604/358 |
| 4,595,392 | A | * | 6/1986 | Johnson et al. | 604/385.17 |
| 4,612,674 | A | * | 9/1986 | Hashimoto | 2/406 |
| 4,911,701 | A | * | 3/1990 | Mavinkurve | 604/385.25 |
| 5,069,676 | A | * | 12/1991 | Ito et al. | 604/358 |
| 5,423,786 | A | * | 6/1995 | Fung et al. | 604/367 |
| 5,518,801 | A | * | 5/1996 | Chappell et al. | 428/152 |
| 5,520,675 | A | * | 5/1996 | Knox-Sigh | 604/385.17 |
| 5,591,148 | A | * | 1/1997 | McFall et al. | 604/378 |
| 5,591,150 | A | * | 1/1997 | Olsen et al. | 604/385.23 |
| 5,665,081 | A | * | 9/1997 | Grosse | 604/359 |
| 5,833,680 | A | * | 11/1998 | Hartman | 604/385.17 |
| 5,853,401 | A | * | 12/1998 | Mayer et al. | 604/378 |
| 5,873,869 | A | * | 2/1999 | Hammons et al. | 604/385.01 |
| 5,895,381 | A | * | 4/1999 | Osborn, III | 604/385.17 |
| 5,957,909 | A | * | 9/1999 | Hammons et al. | 604/387 |
| 6,127,595 | A | * | 10/2000 | Makoui et al. | 604/367 |
| 6,231,555 | B1 | * | 5/2001 | Lynard et al. | 604/385.01 |
| 6,312,416 | B1 | * | 11/2001 | Brisebois et al. | 604/385.01 |
| 6,316,688 | B1 | * | 11/2001 | Hammons et al. | 604/378 |

(Continued)

FOREIGN PATENT DOCUMENTS

JP 11-500940 1/1999

(Continued)

*Primary Examiner*—Tatyana Zalukaeva
*Assistant Examiner*—Paula L Craig
(74) *Attorney, Agent, or Firm*—Darby & Darby P.C.

(57) ABSTRACT

A sanitary napkin includes a napkin body containing a liquid absorbent layer and a three-dimensional structure is disposed on the skin-side surface of the napkin body. The three-dimensional structure is formed of an air-laid nonwoven fabric and a liquid-permeable sheet, and the air-laid nonwoven fabric is formed with upwardly extending compressed portions. The three-dimensional structure comes into close contact with the body's groove to effectively prevent lateral leakage of menstrual blood during sleep.

16 Claims, 9 Drawing Sheets

U.S. PATENT DOCUMENTS

| | | | |
|---|---|---|---|
| 6,348,047 B1 * | 2/2002 | Harper | 604/385.17 |
| 6,350,257 B1 * | 2/2002 | Bjorklund et al. | 604/385.01 |
| 6,350,258 B1 * | 2/2002 | Markowiecki | 604/385.201 |
| 6,394,989 B2 * | 5/2002 | Mizutani | 604/385.01 |
| 6,398,770 B1 * | 6/2002 | Drevik | 604/385.01 |
| 6,410,822 B1 * | 6/2002 | Mizutani | 604/380 |
| 6,413,248 B1 * | 7/2002 | Mizutani | 604/385.17 |
| 6,448,466 B1 * | 9/2002 | Ribeiro de Carvalho | 604/378 |
| 6,471,682 B2 * | 10/2002 | Kashiwagi | 604/385.27 |
| 6,475,199 B1 * | 11/2002 | Gann et al. | 604/385.01 |
| 6,579,272 B1 * | 6/2003 | Samuelsson et al. | 604/385.01 |
| 6,586,076 B1 * | 7/2003 | Mizutani et al. | 428/173 |
| 6,613,031 B2 * | 9/2003 | Glasgow et al. | 604/385.03 |
| 6,632,210 B1 * | 10/2003 | Glasgow et al. | 604/385.17 |
| 6,652,503 B1 * | 11/2003 | Bradley | 604/385.17 |
| 6,656,170 B2 * | 12/2003 | Osterdahl et al. | 604/385.17 |
| 6,680,423 B1 * | 1/2004 | Tanzer | 604/380 |
| 6,890,326 B2 * | 5/2005 | White | 604/385.17 |
| 6,913,573 B1 * | 7/2005 | Viscomi et al. | 600/29 |
| 6,932,801 B1 * | 8/2005 | Samuelsson | 604/385.17 |
| 6,964,655 B2 * | 11/2005 | Killeen et al. | 604/385.04 |
| 6,974,892 B2 * | 12/2005 | DeCarvalho et al. | 604/380 |
| 6,997,915 B2 * | 2/2006 | Gell et al. | 604/385.16 |
| 7,078,583 B2 * | 7/2006 | Kudo et al. | 604/380 |
| 7,145,054 B2 * | 12/2006 | Zander et al. | 604/380 |
| 2001/0000796 A1 * | 5/2001 | Osborn et al. | 604/385.17 |
| 2002/0068915 A1 * | 6/2002 | Drevik et al. | 604/385.01 |
| 2002/0077614 A1 * | 6/2002 | Molas et al. | 604/385.01 |
| 2003/0083639 A1 * | 5/2003 | Killeen et al. | 604/389 |
| 2004/0131820 A1 * | 7/2004 | Turner et al. | 428/92 |
| 2004/0147898 A1 * | 7/2004 | Mizutani et al. | 604/385.17 |
| 2004/0162537 A1 * | 8/2004 | Manasek | 604/385.01 |
| 2004/0254554 A1 * | 12/2004 | Mavinkurve et al. | 604/380 |
| 2004/0267220 A1 * | 12/2004 | Hull et al. | 604/380 |
| 2005/0267433 A1 * | 12/2005 | Tanio et al. | 604/385.17 |
| 2005/0267434 A1 * | 12/2005 | Tanio et al. | 604/385.17 |
| 2006/0142723 A1 * | 6/2006 | Kuroda et al. | 604/385.04 |
| 2006/0142724 A1 * | 6/2006 | Watanabe et al. | 604/385.04 |
| 2006/0142725 A1 * | 6/2006 | Fujikawa et al. | 604/385.04 |

FOREIGN PATENT DOCUMENTS

| | | |
|---|---|---|
| JP | 11-42250 | 2/1999 |
| JP | 2001-504727 | 4/2001 |
| JP | 2002-512851 | 5/2002 |

* cited by examiner

SANITARY NAPKIN HAVING THREE-DIMENSIONAL STRUCTURE IN INTERGLUTEAL CLEFT-FACING REGION

This application claims priority to Japanese patent application No. 2004-156959 filed May 27, 2004.

BACKGROUND OF THE INVENTION

1. Field of the Invention

The present invention relates to an elongated sanitary napkin having a vagina-facing region and an intergluteal cleft-facing region elongated rearward thereof and more particularly to a sanitary napkin which can be kept in close contact with the intergluteal cleft, which extends posteriorly from the anus of the body, and can also follow the deformation of the intergluteal cleft so as to be effective in preventing rearward leakage of menstrual blood during sleep.

2. Description of the Related Art

Conventional sanitary napkins include ones having a protruding structure, which is intended to come into close contact with the wearer's body, on a skin-side surface of a napkin body containing a liquid absorbent layer.

Patent Publication 1 identified below discloses a sanitary napkin including a primary absorbent member of a triangular cross-section. This primary absorbent member is composed of an absorbent core for absorption and retention of liquid and an outer cover covering the absorbent core. In this sanitary napkin disclosed in Patent Publication 1, the primary absorbent member comes into close contact with the vaginal opening so that menstrual blood can be mainly absorbed and retained by the primary absorbent member. The sanitary napkin also includes a secondary absorbent member which is flat and intended to come into contact with garments and the primary absorbent member is disposed on the secondary absorbent member.

Patent Publication 2 discloses a sanitary napkin including a tube of absorbent material having a function of absorbing liquid. This tube of absorbent material is composed of an absorbent material shaped into a tube and a cover covering the absorbent material and therefore the tube of absorbent material is allowed to comfortably fit to the vaginal opening of a wearer. Here, the tube of absorbent material is disposed on a base pad.

Patent Publication 3 identified below discloses a hump of a triangular cross-section bulging from a skin-side surface of a sanitary napkin. This hump is composed of an absorbent body and a stiffening element disposed between a liquid-permeable topsheet and a liquid absorbent layer, and the stiffening element is formed of a rigid material such as a plastic sheet. In the sanitary napkin disclosed in Patent Publication 3, even when the hump reinforced by the stiffening element comes into contact with the vaginal opening and is subjected to a compressive force due to body pressure, the hump can keep the sanitary napkin in close contact with the vaginal opening without being crushed down.

Patent Publication 3 also discloses in FIG. 5 an embodiment in which the stiffening element formed of a plastic sheet has a raised portion at its rear end and describes that the raised portion can fit in the intergluteal cleft.

Patent Publication 4 identified below discloses a sanitary napkin having a heaped protrusion in a rear region of a skin-side surface. From the description of Patent Publication 4, it is unclear how the protrusion is constituted, but it describes that the protrusion comes into contact with the cleft of the buttocks to prevent rearward leakage of menstrual blood.

Patent Publication 1: Japanese Unexamined Patent Publication No. H11-500940

Patent Publication 2: Japanese Unexamined Patent Publication No. 2002-512851

Patent Publication 3: Japanese Unexamined Patent Publication No. 2001-504727

Patent Publication 4: Japanese Unexamined Patent Publication No. H11-42250

For sanitary napkins to be worn by women during sleep, there have been known elongated sanitary napkins in which a buttocks-facing region is formed behind a vagina-facing region. However, menstrual blood trying to flow down the intergluteal cleft posteriorly during sleep cannot be effectively blocked only by applying the rear portion of the sanitary napkin to the buttocks.

The sanitary napkin of Patent Publication 1 has the primary absorbent member of a triangular cross-section, and the sanitary napkin disclosed in Patent Publication 2 has the tube of absorbent material. However, the primary absorbent member and the tube of absorbent material, which are both aimed to comfortably fit to the vaginal opening of women, are not intended to face the intergluteal cleft. Even if the primary absorbent member and the tube of absorbent material face the intergluteal cleft, since they are insufficient in stiffness to enter the intergluteal cleft, they cannot closely fit in the intergluteal cleft.

In the sanitary napkin disclosed in Patent Publication 3, on the other hand, the stiffening element prevents the hump from being easily crushed down. Although Patent Publication 3 discloses providing the raised portion at the rear end of the stiffening element for a fit into the intergluteal cleft, since the stiffening element is a stiff member such as a plastic sheet, the stiff member is liable to give an unpleasant feeling to the intergluteal cleft. In detail, the depth of the intergluteal cleft varies between the standing position and the supine position and the cleft becomes shallow in the lying position due to close contact between the opposing surfaces of the buttocks. When a wearer takes the supine position with the hump, which is reinforced by the stiff member, being positioned to face the intergluteal cleft, the stiff member hits the shallow cleft of the buttocks to easily give an unpleasant feeling, which leads to restlessness in sleep.

In the sanitary napkin disclosed in Patent Publication 4, the construction of the protrusion remains unclear, but this protrusion has a triangular cross-section and is not allowed to easily fit in the intergluteal cleft like those in Patent Publications 1 and 2.

SUMMARY OF THE INVENTION

The present invention has been developed to solve the problems in the prior art set forth above and has an object to provide a sanitary napkin in which a three-dimensional structure located on its skin-side surface is enabled to closely fit in the intergluteal cleft so as to be effective in preventing rearward leakage of menstrual blood during sleep.

According to the invention, there is provided an elongated sanitary napkin comprising a napkin body containing a liquid absorbent layer for absorption and retention of liquid and having a vagina-facing region and an intergluteal cleft-facing region rearward of the vagina-facing region, wherein a three-dimensional structure is provided in the intergluteal cleft-facing region to bulge from a skin-side surface of the napkin body with an apex spaced from the skin-side surface, and the three-dimensional structure has a liquid-permeable sheet which is exposed externally and a reinforcing member which is located beneath the liquid-permeable sheet, wherein the reinforcing member is enabled to be elastically deformed to reduce a height of the three-dimensional structure when a pressure toward the napkin body is exerted on the apex of the three-dimensional structure.

In the sanitary napkin according to the present invention, the three-dimensional structure is provided in the intergluteal cleft-facing region, wherein the reinforcing member secures stiffness of the three-dimensional structure and also allows the three-dimensional structure to be deformed to reduce a height when a body pressure is exerted on the apex. Accordingly, the three-dimensional structure can closely fit in the intergluteal cleft without giving an unpleasant feeling, thereby blocking menstrual blood trying to flow down the intergluteal cleft posteriorly.

In the invention, preferably, the three-dimensional structure has front and rear starting points from which the three-dimensional structure starts to bulge from the skin-side surface of the napkin body, the three-dimensional structure having a maximum bulging height from the skin-side surface at a location midway between the front and rear starting points, the location where the bulging height is maximum being located on or rearward of an anus-facing region of the napkin body.

In this construction, since the location where the three-dimensional structure has a maximum height can face the deepest part of the intergluteal cleft, the three-dimensional structure closely fits into the intergluteal cleft to easily prevent rearward leakage of menstrual blood.

In the invention, preferably, when a pressure in a direction perpendicular to the skin-side surface of the napkin body is applied to the apex of the three-dimensional structure at the location where the three-dimensional structure has a maximum height and the pressure reaches 0.2 N per unit area of the apex having a width of 1 mm and a length of 10 mm, a reduction in height at the apex is equal to or less than 66%.

The minimum load required to insert the three-dimensional structure into the intergluteal cleft as far as it will go is 0.2 N per unit area having a width of 1 mm and a length of 10 mm. On the other hand, when a woman alters her position from the standing position to the supine position, the maximum reduction in depth of the body's groove is about 66%. Accordingly, if the height of the three-dimensional structure does not reduce more than 66% when a force of 0.2 N is exerted thereon, the three-dimensional structure can be kept in close contact with the body's groove in the supine position.

In the invention, also preferably, when a pressure in a direction perpendicular to the skin-side surface of the napkin body is applied to the apex of the three-dimensional structure at the location where the three-dimensional structure has a maximum height and the pressure reaches 0.3 N per unit area of the apex having a width of 1 mm and a length of 10 mm, a reduction in height at the apex is equal to or greater than 20%.

When a woman alters her position from the standing position to the supine position, the reduction in depth of the intergluteal cleft is about 20%. On the other hand, a load applied to the buttocks hardly gives an unpleasant feeling to the buttocks if the force is equal to or less than 0.3 N per unit area having a width of 1 mm and a length of 10 mm. Accordingly, if the height can reduce 20% or more when a force of 0.3 N is exerted on the apex of the three-dimensional structure, the three-dimensional structure can follow the deformation of the intergluteal cleft in the supine position without giving an unpleasant feeling to the wearer's body.

In the invention, also preferably, the reinforcing member is a fibrous layer which has a function of absorbing liquid and is in close contact with the liquid-permeable sheet inside the three-dimensional structure.

By employing the fibrous layer for the reinforcing member, it becomes easy to set the stiffness of the three-dimensional structure to such a degree that the three-dimensional structure can be kept in close contact with the intergluteal cleft without giving an unpleasant feeling and can follow the deformation of the intergluteal cleft as set forth above.

Also preferably, the three-dimensional structure is hollow. If the three-dimensional structure is hollow, opposing walls are allowed to be easily deformed to facilitate a fit of the three-dimensional structure into the intergluteal cleft.

Also in the invention, the fibrous layer forming the reinforcing member is preferably formed with compressed portions, and the compressed portions preferably extend linearly in a direction away from the skin-side surface of the napkin body.

Formation of such compressed portions results in increasing the stiffness of the three-dimensional structure so that the three-dimensional structure can fit in the intergluteal cleft without giving an unpleasant feeling.

Also in the invention, the three-dimensional structure may be narrower in width in an intermediate portion than in front and rear portions so that the intermediate portion can easily fit in the intergluteal cleft.

Also in the invention, the three-dimensional structure may be shaped to gradually decrease in width from a base adjacent to the skin-side surface toward the apex. In this construction, the three-dimensional structure preferably has a base width of 15 to 45 mm and an apex width of 1 to 5 mm.

If the width of the three-dimensional structure is gradually decreased toward the apex, the three-dimensional structure can easily fit in the intergluteal cleft.

According to the present invention, the three-dimensional structure provided on the skin-side surface of the napkin body easily comes in close contact with the intergluteal cleft. In addition, even when a woman alters her position from the standing position to the supine position, the three-dimensional structure can be easily kept in close contact with the intergluteal cleft without giving an unpleasant feeling to the wearer's body. Therefore, menstrual blood trying to flow down the intergluteal cleft posteriorly can be easily blocked to prevent rearward leakage of menstrual blood.

DESCRIPTION OF THE PREFERRED EMBODIMENT

Figure 1:
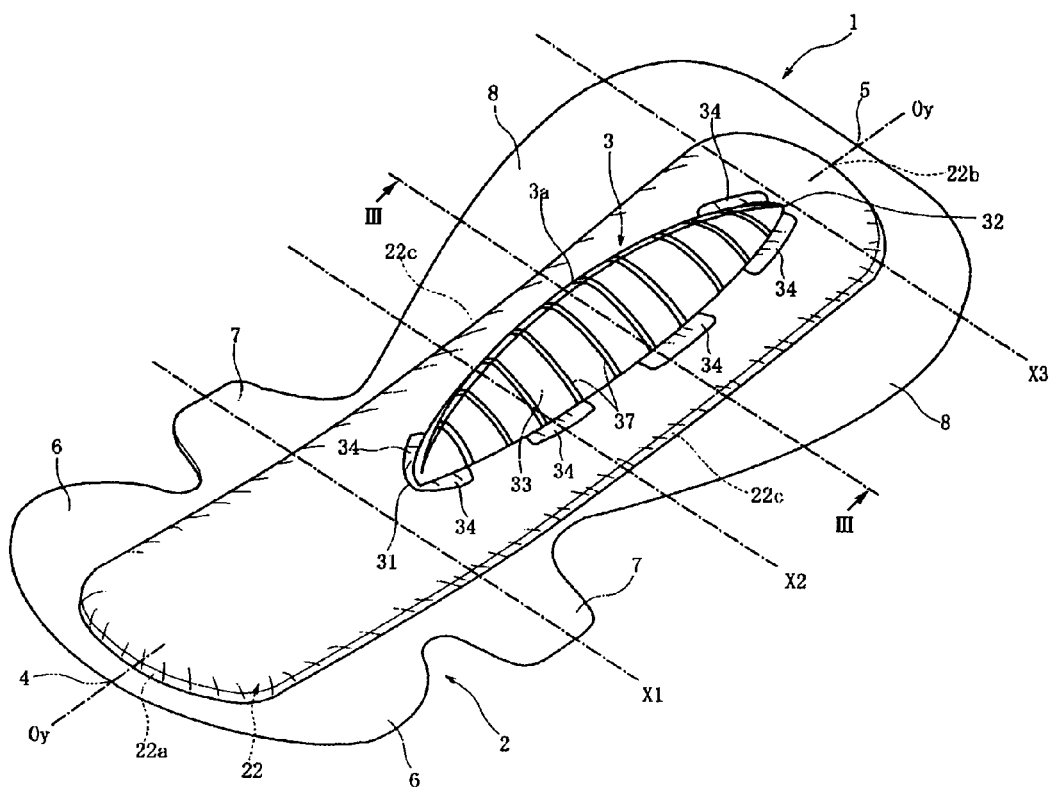
FIG. 1 is a perspective view showing a sanitary napkin according to a first embodiment of the invention.
Figure 2:
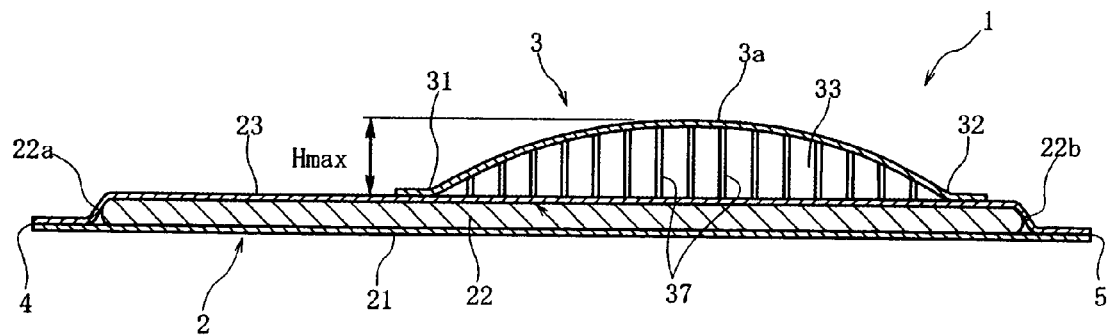
FIG. 2 is a longitudinal sectional view of the sanitary napkin.
Figure 3:
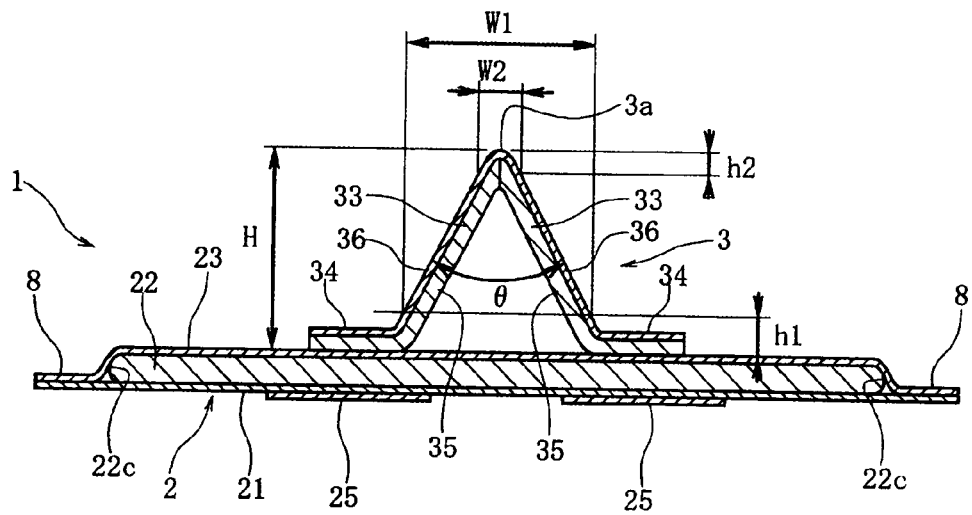
FIG. 3 is a sectional view of the sanitary napkin of FIG. 1 taken along line III-III.

FIG. 1 is a perspective view showing a sanitary napkin 1 according to a first embodiment of the invention, FIG. 2 is a longitudinal sectional view of the sanitary napkin 1, and FIG. 3 is a transverse sectional view of the sanitary napkin 1 of FIG. 1 taken along line III-III.

It should be noted that the sanitary napkin, as well as its individual components, has two major surfaces: of which one surface intended to be worn toward the wearer's crotch is referred to as "skin-side surface", while the other surface is referred to as "garment-side surface". In addition, the lengthwise direction of the sanitary napkin is referred to as "longitudinal direction", while the direction perpendicular to the longitudinal direction is referred to as "width direction". With respect to dimensions of the individual components, unless otherwise stated, a dimension measured in the longitudinal direction is referred to as "length", while a dimension measured in the width direction is referred to as "width".

The sanitary napkin 1 according to the first embodiment comprises a napkin body 2 and a three-dimensional structure 3 located on the skin-side surface of the napkin body 2.

As shown in FIGS. 2 and 3, the napkin body 2 comprises a liquid blocking backsheet 21 on its garment-side surface, a liquid absorbent layer 22 disposed on it, and a liquid-permeable topsheet 23 covering the liquid absorbent layer 22.

As shown in FIG. 1, the napkin body 2 has a curved front end 4, as well as a curved rear end 5. The napkin body 2 is elongated to have a maximum length of 280 to 450 mm. The liquid absorbent layer 22 is also elongated, and the liquid absorbent layer 22 has a curved front end 22a spaced slightly inward from the front end 4 and a curved rear end 22b spaced slightly inward from the rear end 5. On the other hand, left and right side ends 22c, 22c of the liquid absorbent layer 22 extend linearly in parallel relationship with a longitudinal centerline Oy.

The napkin body 2 has front flaps 6, 6, fold-back flaps 7, 7 and rear flaps 8, 8 which project from the side ends 22c, 22c of the liquid absorbent layer 22. Here, the fold-back flaps 7, 7 are located rearward of the front flaps 6, 6 and the rear flaps 8, 8 are located rearward of the fold-back flaps 7, 7. In the front flaps 6, 6, fold-back flaps 7, 7 and rear flaps 8, 8, the backsheet 21 and the topsheet 23 overlap with each other and are bonded to each other through a hot-melt type adhesive. Alternatively, liquid blocking side sheets may be provided on the skin-side surface of the napkin body to cover both sides thereof so that the backsheet 21 and the side sheets constitute the front flaps 6, 6, fold-back flaps 7, 7 and rear flaps 8, 8.

The backsheet 21 may be a film, for example, a polyethylene resin film having a basis weight of about 23 g/m$^2$, and is preferably permeable to moisture. The liquid absorbent layer 22 may be a mixture of fluff pulp and superabsorbent polymer (SAP) wrapped in a hydrophilic tissue, wherein the fluff pulp has a weight of about 400 g/m$^2$.

The topsheet 23 may be a through-air bonded nonwoven fabric having a basis weight of about 25 g/m$^2$. Constituent fibers of the through-air bonded nonwoven fabric may be sheath/core bicomponent synthetic fibers, of which the core is polyethylene terephthalate resin and the sheath is polyethylene resin and the core is mixed with an inorganic filler such as titanium oxide.

The liquid-permeable topsheet 23 may be a point-bonded nonwoven fabric, a spunlaced nonwoven fabric or a spun-bonded nonwoven fabric, without limited to the through-air bonded nonwoven fabric, but its fiber density is preferably equal to or less than 0.12 g/cm$^3$ so as to improve liquid permeability. Alternatively, the topsheet 23 may be a resin film formed with a large number of liquid passage apertures.

X1 shown in FIG. 1 represents a vagina-facing reference line and this vagina-facing reference line X1 is spaced 100 to 200 mm rearwardly from the front end 4 of the napkin body 2, for example, spaced about 150 mm rearwardly from the front end 4.

The vagina-facing reference line X1 as used herein is a target position with which the center of the vaginal opening is to almost coincide when the sanitary napkin 1 is fixed to an undergarment and worn in the crotch. Leading to this target is through the contour of the sanitary napkin as viewed from the skin side or the whole design including the shape of compression lines on the skin-side surface, and particularly when the fold-back flaps 7, 7 are provided as in the present embodiment, the longitudinal centers of the fold-back flaps 7, 7 usually coincide with the target with which the center of the vaginal opening is to coincide.

In the present embodiment, accordingly, the line passing through the centers of the fold-back flaps 7, 7 is taken as the vagina-facing reference line X1.

X2 shown in FIG. 1 represents an anus-facing reference line and this anus-facing reference line X2 is intended to face the anus when the vagina-facing reference line X1 coincides with the center of the vaginal opening. The anus-facing reference line X2 is usually spaced a distance of 30 to 70 mm, which varies depending on the wearer's body, rearwardly from the vagina-facing reference line X1.

X3 shown in FIG. 1 represents a coccyx-facing reference line. This coccyx-facing reference line X3 is intended to face the coccyx when the vagina-facing reference line X1 coincides with the center of the vaginal opening. The coccyx-facing reference line X3 is usually spaced a distance of 120 to 180 mm, which varies depending on the wearer's body, rearwardly from the vagina-facing reference line X1. The rear end 5 of the napkin body 2 and the rear end 22b of the liquid absorbent layer 22 are located rearward of the coccyx-facing reference line X3.

In the crotch of a woman, a "body's groove" extends from the anterior end of the vagina (the anterior end of the labia) to the coccyx, and of the "body's groove", the portion from adjacent the anus to the coccyx is referred to as "intergluteal cleft" throughout the description. In the sanitary napkin 1 of FIG. 1, the area within 50 mm forward and rearward from the vagina-facing reference line X1 is referred to as vagina-facing region, while the area from the anus-facing reference line X2 to the coccyx-facing reference line X3 is referred to as intergluteal cleft-facing region.

Figure 11:
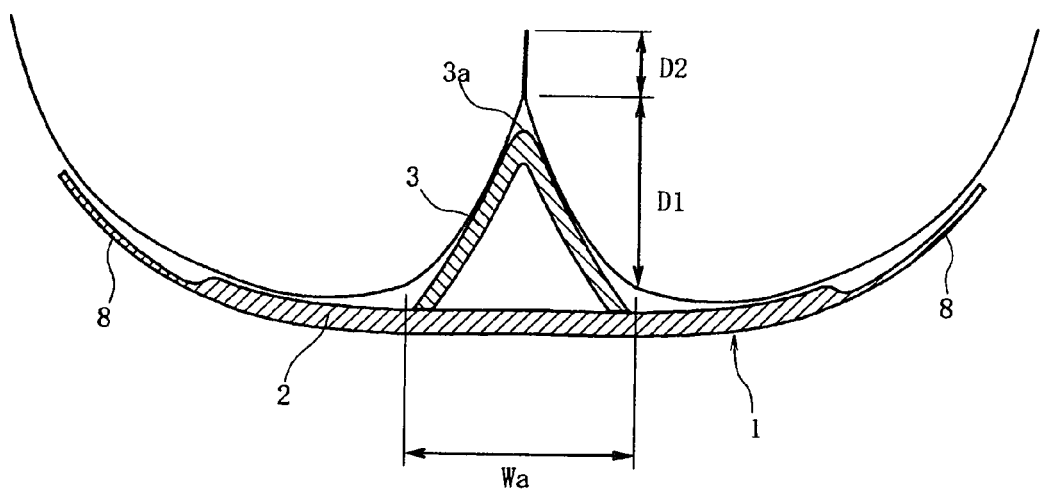
FIG. 11 is a sectional view taken along line XI-XI of FIG. 10.

FIG. 11 schematically shows the body's groove. The body's groove has a noncontact portion where the opposing surfaces of the buttocks are separated from each other and a contact portion where the opposing surfaces of the buttocks are in close contact with each other. In FIG. 11, the depth of the noncontact portion is indicated by D1, while the depth of the contact portion is indicated by D2. It should be noted that the depth D1 of the noncontact portion is measured for the standing position with a reference point positioned at a level where the distance Wa between the opposing surfaces of the buttocks is 40 mm and also measure for the supine position with a reference point positioned at a level where the distance Wa is 30 mm.

Figure 10:
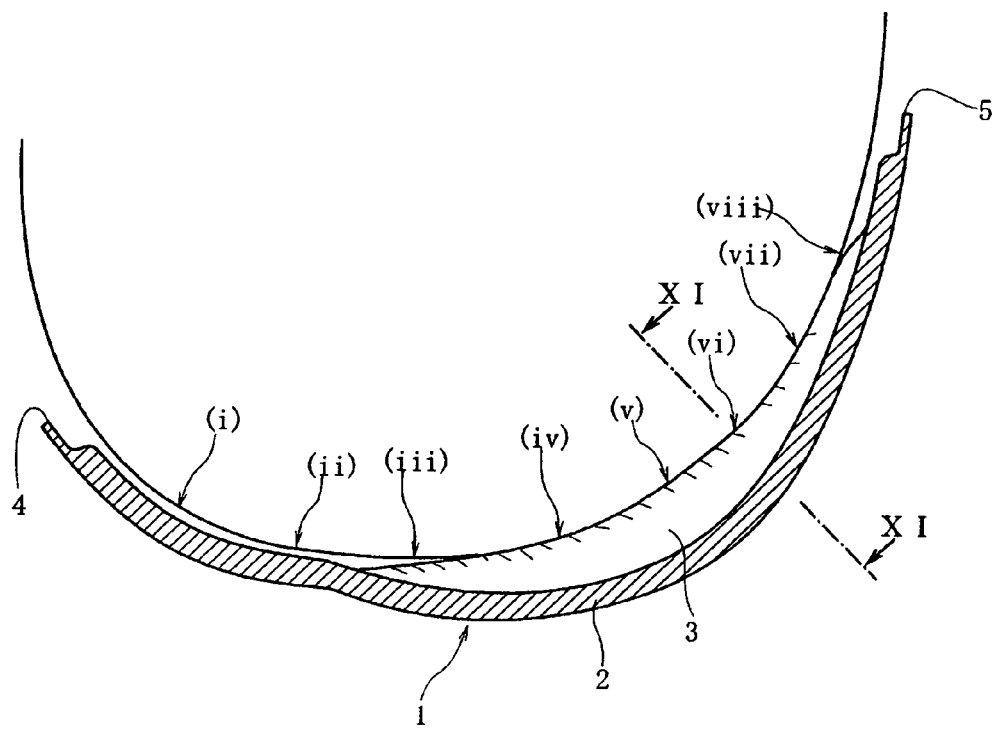
FIG. 10 is a longitudinal sectional view showing a state where the sanitary napkin of the present invention is worn in the crotch of a woman.

FIG. 10 is a longitudinal sectional view showing a state where the sanitary napkin 1 is worn in the crotch of a woman. In the woman's body, (i) represents a location 20 mm anterior of the center of the vaginal opening, and (ii) represents the center of the vaginal opening. (iii) represents the posterior commissure of labia majora which is located 50 mm posterior of the center of the vaginal opening. In addition, (iv) represents the anus, (v) represents a location 25 mm posterior of the anus, (vi) represents a location 50 mm posterior of the anus, (vii) represents a location 80 mm posterior of the anus, and (viii) represents the coccyx.

Figure 12:
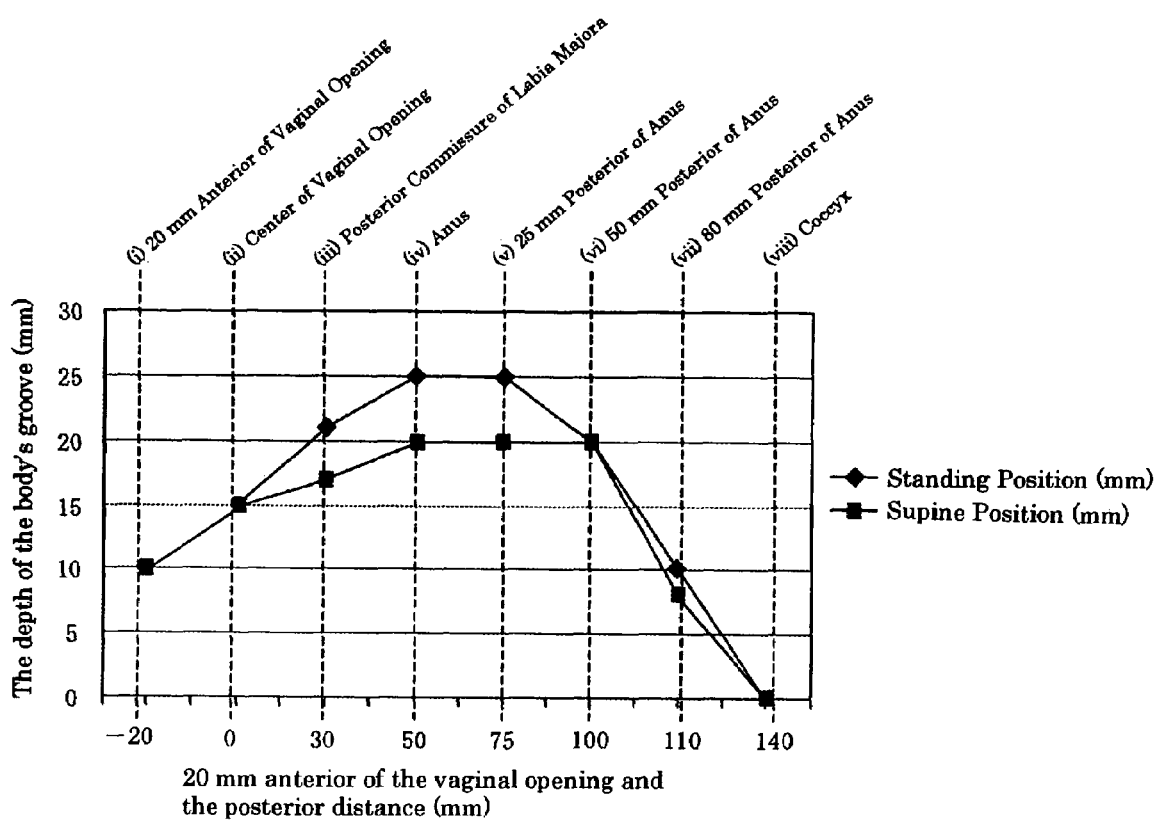
FIG. 12 is a diagram where the depth of the body's groove is measured for a woman.

FIG. 12 shows measured values of the depth D1 of the noncontact portion at the locations (i) to (viii). These values were measured for a Japanese woman who is 27 years old, weights 56 Kg, stands 168 cm tall and has a BMI of 19.8.

As shown in FIG. 12, the depth D1 of the noncontact portion in the body's groove is brought to a maximum between the anus (iv) and the location (v) 25 mm posterior of the anus, and the maximum depth is about 25 mm in the standing position and about 20 mm in the supine position.

In the sanitary napkin 1 of FIG. 1, the three-dimensional structure 3 is provided on a rear portion of the napkin body 2. The three-dimensional structure 3 is intended to closely fit in the noncontact portion, more preferably make its way into the contact portion, at least within the range from the anus (iv) to the location (vi) 50 mm posterior of the anus in the body's groove. Therefore, the three-dimensional structure 3 extends at least 50 mm rearwardly from the anus-facing reference line X2.

In the sanitary napkin 1 of FIG. 1, the three-dimensional structure 3 has a front starting point 31 which is located forward of the anus-facing reference line X2 and slightly rearward of the vagina-facing reference line X1. It also has a rear starting point 32 which is located slightly forward of the coccyx-facing reference line X3. It should be noted that the front starting point 31 may be located anywhere within the range from a location 20 mm forward of the vagina-facing reference line X1 to the anus-facing reference line X2.

H shown in FIG. 3 represents a height from the skin-side surface of the napkin body 2 to an apex 3a of the three-dimensional structure 3. The height H gradually increases toward the center from the front and rear starting points 31, 32 so that the apex 3a, which extends along the longitudinal centerline Oy of the napkin body 2, is curved away from the skin-side surface of the napkin body 2, as shown in FIG. 2. Preferably, the apex 3a provides a maximum height $H_{max}$ at a location where the intergluteal cleft becomes deepest, i.e., within the range from the anus-facing reference line X2 to the location 50 mm rearward of it. In the present embodiment, the maximum height $H_{max}$ is provided at the location 50 mm rearward of the anus-facing reference line X2.

As shown in FIG. 3, the three-dimensional structure 3 has a pair of walls 33, 33 which extend in the longitudinal direction on opposite sides. The width between the walls 33, 33 gradually decreases from a base adjacent to the skin-side surface of the napkin body 2 toward the apex 3a. The three-dimensional structure 3 has a base width W1 which is measured at a level spaced from the skin-side surface of the napkin body 2 by h1=10 mm, and the base width W1 is preferably in the range of 15 to 45 mm. The distance Wa is 30 to 40 mm in the standing position and 20 to 30 mm in the supine position. If the base width W1 is in the range of 15 to 45 mm, the three-dimensional structure 3 can enter the intergluteal cleft without giving an unpleasant feeling.

The three-dimensional structure 3 also has an apex width W2 which is measured at a level spaced from the apex 3a of the three-dimensional structure 3 by h2=3 mm, and the apex width W2 is preferably in the range of 1 to 5 mm, more preferably in the range of 1 to 3 mm. If the apex width W2 is within the range, the apex 3a can reach the deepest part of the body's groove, and particularly if the apex width W2 is equal to or greater than 1 mm, the apex 3a becomes less irritating to the body's groove even when it comes into contact with the deepest part of the body's groove.

The walls 33, 33 of the three-dimensional structure 3 form an opening angle θ which is equal to or less than 120 degrees, preferably equal to or less than 90 degrees. More preferably, it is equal to or less than 60 degrees or 45 degrees. It should be noted that when the three-dimensional structure 3 has a triangular cross-section as shown in FIG. 3, the opening angle θ is an angle between the outer surfaces of the walls 33, 33. On the other hand, when the outer surfaces of the walls 33, 33 are outwardly curved to bulge laterally in the cross-section of FIG. 3, the opening angle θ is an angle between tangents to the outer surfaces of the walls 33, 33 at one half the height from the skin-side surface of the napkin body 2 to the apex 3a.

Here, the measurement of the angle θ is carried out using a measurement jig whose cylindrical inner surface has a radius of 110 mm such that the garment-side surface of the sanitary napkin 1 is adhered to the cylindrical inner surface with the longitudinal direction of the sanitary napkin 1 being oriented along the direction of curvature of the cylindrical inner surface. Then, the angle θ is measured at a location where the bulging height of the three-dimensional structure 3 from the skin-side surface of the napkin body 2 is brought to a maximum.

Here, the cross-sectional shape of the three-dimensional structure 3 is not limited to the triangle shown in FIG. 3; for example, the apex 3a may be flattened or the walls 33, 33 may be bulged laterally outwardly to have curved surfaces.

At their lower ends, as shown in FIGS. 1 and 3, the walls 33, 33 of the three-dimensional structure 3 are integrally formed with joining members 34, and the joining members 34 are bonded to and fixed on the skin-side surface of the napkin body 2 through a hot-melt type adhesive. In the present embodiment, the three-dimensional structure 3 is so fixed as not to be removable from the skin-side surface throughout the length. However, the three-dimensional structure 3 may be fixed on the skin-side surface exclusively at locations adjacent the front and rear starting points 31, 32 so as to allow the intermediate portion to be freely movable in the width direction with respect to the skin-side surface. With this construction, the three-dimensional structure 3 can be easily kept in close contact with the intergluteal cleft even when the napkin body 2 moves laterally together with an undergarment.

As shown in FIG. 3, the three-dimensional structure 3 is composed of a reinforcing member 35 and a liquid-permeable sheet 36 covering the skin-side surface of the reinforcing member 35. The reinforcing member 35 has not only a function of increasing stiffness but also a function of absorbing and retaining liquid. Here, the three-dimensional structure 3 is hollow.

For the reinforcing member 35, there may be used an air-laid nonwoven fabric. The air-laid nonwoven fabric may be produced such that 30 wt. % of pulp fibers and 70 wt. % of sheath/core bicomponent synthetic fibers (core is polypropylene resin; sheath is polyethylene resin) are blended, deposited by the air-laid process, and pressed between heating rollers to be bonded together through a bonding force of the polyethylene resin when subjected to heat.

For the reinforcing member 35, two or three sheets of the air-laid nonwoven fabric may be stacked to have a basis weight of about 60 to 300 g/m². The reinforcing member 35 is also heated under pressure by embossing to have compressed portions 37. As shown in FIGS. 1 and 2, the compressed portions 37 are spaced in the longitudinal direction and parallel to each other to extend upward from the skin-side surface of the napkin body 2 to the apex 3a in a direction substantially perpendicular to the longitudinal direction.

In FIG. 3, the walls 33, 33 are separately formed of the reinforcing member 35, bonded to each other at the apex 3a through a hot-melt type adhesive and then covered with the single liquid-permeable sheet 36. The liquid-permeable sheet 36 may be a through-air bonded nonwoven fabric of heat-fusible synthetic resin fibers, and the liquid-permeable sheet 36 and the reinforcing member 35 are bonded to each other through a hot-melt type adhesive applied to such an extent as not to interfere with liquid passage.

The liquid-permeable sheet 36 may be a point-bonded nonwoven fabric, a spunlaced nonwoven fabric or a spun-bonded nonwoven fabric, without limited to the through-air bonded nonwoven fabric, but its fiber density is preferably equal to or less than 0.12 g/cm³ so as to improve liquid permeability.

For the reinforcing member 35, alternatively, there may be used a through-air bonded, point-bonded or spunbonded nonwoven fabric of one or more kinds of fibers selected from polyethylene fibers, polypropylene fibers, polyester fibers, polyethylene-polypropylene bicomponent synthetic fibers and polyethylene-polyester bicomponent synthetic fibers. Two or more sheets of the nonwoven fabric may be stacked to have a basis weight, for example, of about 60 to 300 g/m² and bonded together by heat-embossing or through a hot-melt adhesive. The reinforcing member 35 thus made only of synthetic resin fibers allows passage of menstrual blood toward the liquid absorbent layer 22, and moreover because the reinforcing member 35 itself is resistant to absorption and retention of menstrual blood, menstrual blood is less apt to remain in the three-dimensional structure 3, so that the three-dimensional structure 3 is prevented from feeling sticky to the skin and provides an improved touch when in contact with the intergluteal cleft.

On the garment-side surface of the napkin body 2, as shown in FIG. 3, pressure-sensitive adhesive layers 25, 25 are disposed on an outer surface of the backsheet 21. The pressure-sensitive adhesive layers 25, 25 are in the shape of strips extending continuously in the longitudinal direction. Preferably, the pressure-sensitive adhesive layers 25, 25 are located beneath the joining members 34 of the three-dimensional structure 3. With this arrangement, the napkin body 2 can be firmly fixed to an undergarment beneath the joining members 34 to keep the three-dimensional structure 3 in close contact with the intergluteal cleft.

Although omitted in the drawings, it should be noted that the fold-back flaps 7, 7 and the rear flaps 8, 8 also have pressure-sensitive adhesive layers on the garment-side surface of the backsheet 21.

When using the sanitary napkin 1, the pressure-sensitive adhesive layers 25, 25 on the garment-side surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment-side surfaces of the fold-back flaps 7, 7 are adhered to the outer side of the crotch part. In addition, the pressure-sensitive adhesive layers on the garment-side surfaces of the rear flaps 8, 8 are adhered to the inner side of the undergarment at a lower part of a back body.

When the sanitary napkin 1 is adhered to the undergarment by a user, the center location between the fold-back flaps 7, 7 (the vagina-facing reference line X1) serves as a target for positioning so that it is worn with the center location almost coinciding with the longitudinal center of the vaginal opening.

FIG. 10 shows a state where the sanitary napkin 1 is worn in the crotch of a woman, and FIG. 11 is a sectional view taken along line XI-XI of FIG. 10 and shows a state where the three-dimensional structure 3 fits in the intergluteal cleft.

The three-dimensional structure 3 is positioned to face at least the intergluteal cleft of the body's groove. As shown in FIG. 3, the three-dimensional structure 3 is so shaped that the width between the walls 33, 33 gradually decreases toward the apex 3a, wherein the apex width W2 is in the range of 1 to 5 mm, preferably in the range of 1 to 3 mm. On the other hand, the opening angle θ between the walls 33, 33 is equal to or less than 120 degrees, preferably equal to or less than 90 degrees, more preferably equal to or less than 60 degrees or 45 degrees.

Accordingly, the three-dimensional structure 3 can easily enter the body's groove from a location slightly posterior of the center of the vaginal opening to a location slightly anterior of the coccyx, which results in close contact of the three-dimensional structure 3 with the noncontact portion of the body's groove, as shown in FIG. 11. In addition, the three-dimensional structure 3 is also enabled to make its way into the contact portion of the intergluteal cleft. In the three-dimensional structure 3, the reinforcing member 35, which is formed of an air-laid nonwoven fabric or the like to have a basis weight in the range of 60 to 300 g/m², is in itself elastic and stiff and is also formed with the compressed portions 37 extending in a direction substantially perpendicular to the longitudinal direction. Hence, the reinforcing member 35 fitting in the intergluteal cleft is less apt to be crushed down. In addition, since the reinforcing member 35 is allowed to be elastically deformed by a pressure exerted on the apex 3a, it can follow the change in the depth of the body's groove and be kept in close contact with the body'groove anteriorly and posteriorly of the body. Furthermore, since the three-dimensional structure 3 is hollow, its width can freely change even when the opposing surfaces of the buttocks approach each other in the body's groove.

Since the three-dimensional structure 3, which is maintained in a three-dimensional shape due to stiffness of the reinforcing member, is not constructed to include a longitudinally extending elastic member in order to be pressed against the wearer's body, it is less apt to give a local pressure or an unpleasant feeling even when the apex 3a of the three-dimensional structure 3 is kept in contact with the deepest part of the body's groove.

When a wearer is in the standing position, for example, menstrual blood discharged from the vaginal opening passes through the topsheet 23 of the napkin body 2 and is then absorbed and retained by the liquid absorbent layer 22. However, menstrual blood trying to move posteriorly along the intergluteal cleft such as during sleep is given to the three-dimensional structure 3 in close contact with the body's groove and then absorbed by the reinforcing member 35 having the function of absorbing liquid after passing through the liquid-permeable sheet 36. If the reinforcing member 35 is formed of an air-laid nonwoven fabric containing synthetic resin fibers in an amount of 70 wt. %, menstrual blood given to the reinforcing member 35 can be readily transferred to the liquid absorbent layer 22. Accordingly, the reinforcing member 35 preferably contains synthetic resin fibers in an amount equal to or greater than 50 wt. %. If the reinforcing member 35 is made only of synthetic resin fibers, as set forth above, menstrual blood is less apt to remain in the three-dimensional structure 3.

Figure 4:
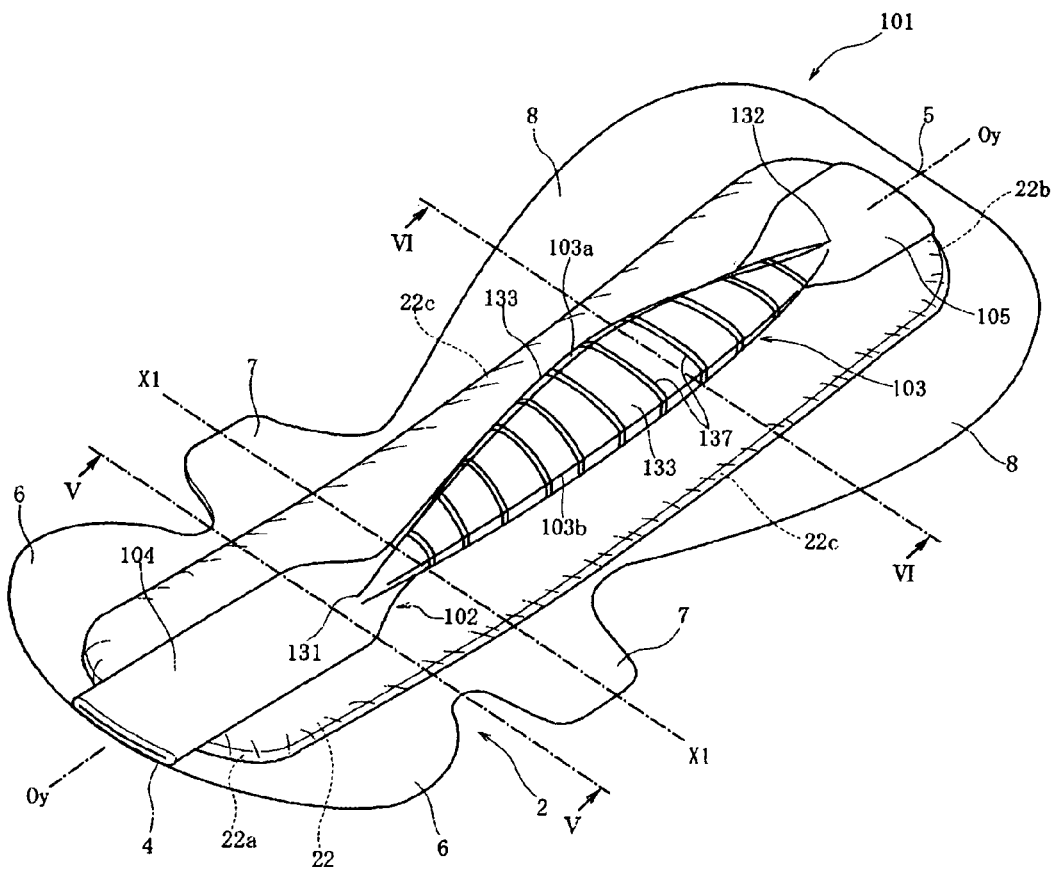
FIG. 4 is a perspective view showing a sanitary napkin according to a second embodiment of the invention.
Figure 5:
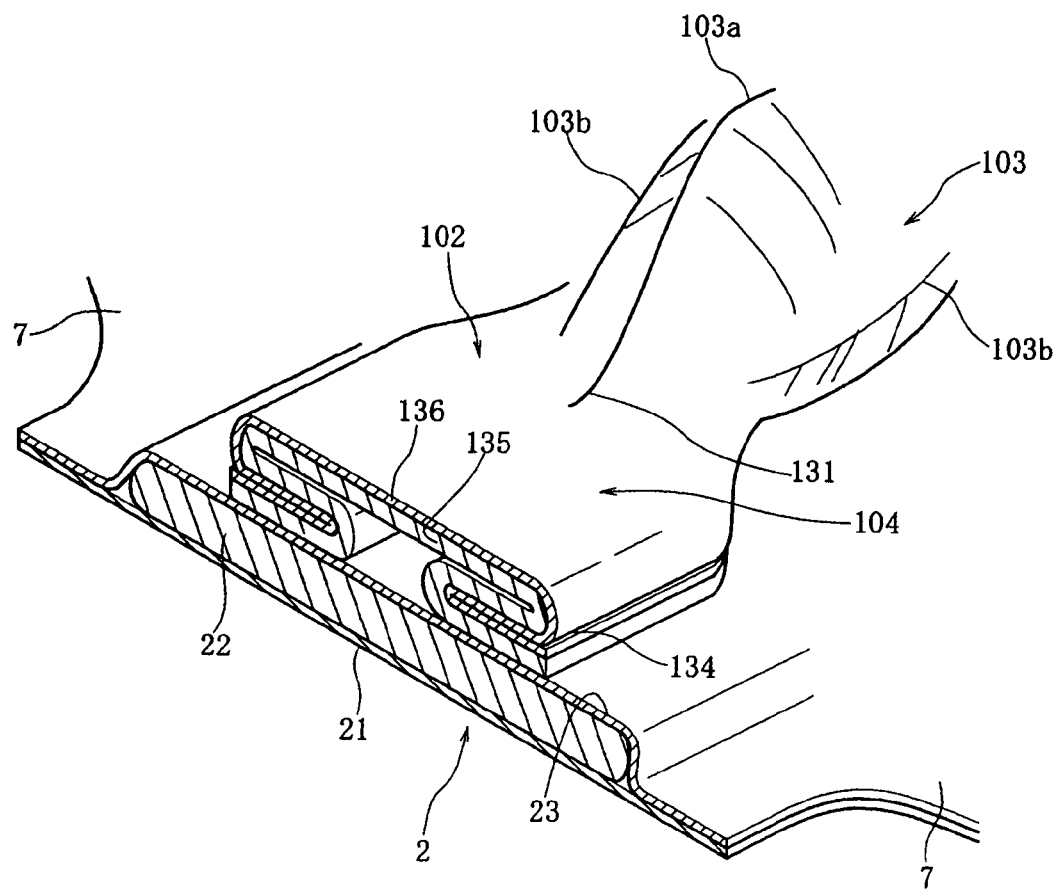
FIG. 5 is a transverse sectional view of the sanitary napkin of FIG. 4 taken along line V-V.
Figure 6:
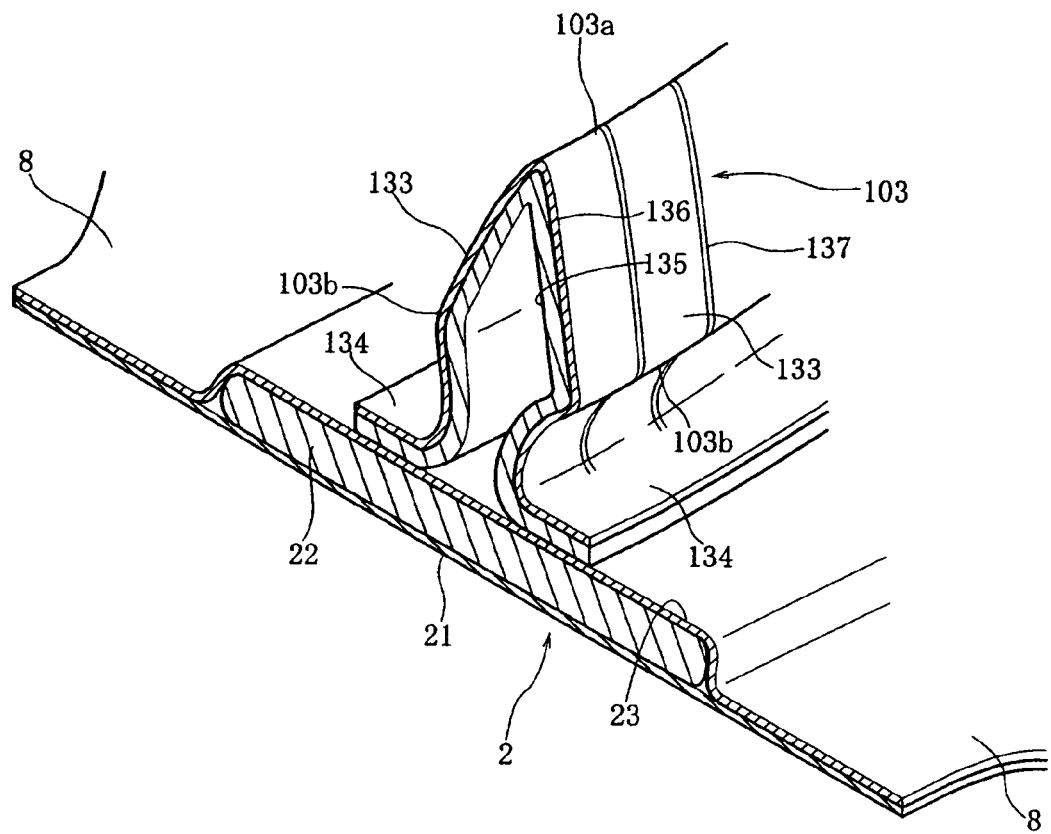
FIG. 6 is a transverse sectional view of the sanitary napkin of FIG. 4 taken along line VI-VI.

FIG. 4 is a perspective view showing a sanitary napkin 101 according to a second embodiment of the present invention, FIG. 5 is a transverse sectional view of the sanitary napkin 101 of FIG. 4 taken along line V-V, and FIG. 6 is a transverse sectional view of the sanitary napkin 101 of FIG. 4 taken along line VI-VI.

The napkin body 2 of FIG. 4 is not changed from the napkin body of the first embodiment shown in FIGS. 1 to 3.

In the second embodiment, a surface element 102 is mounted on the skin-side surface of the napkin body 2 to extend along the longitudinal centerline Oy. As shown in FIGS. 5 and 6, the surface element 102 is composed of a reinforcing member 135 capable of absorbing liquid and permeable to liquid and a liquid-permeable sheet 136 covering the skin-side surface of the reinforcing member 135. The reinforcing member 135 is formed of an air-laid nonwoven fabric of pulp and synthetic resin fibers, wherein the content of the synthetic resin fibers is equal to or greater than 50 wt. %, e.g., 70 wt. %. A single sheet of the air-laid nonwoven fabric may be used or two or more sheets may be stacked to have a total basis weight of about 60 to 300 g/m². In an alternative, the reinforcing member 135 may be formed by joining two or more sheets of a nonwoven fabric made only of synthetic resin fibers, as set forth above.

The liquid-permeable sheet 136 is formed of the same through-air bonded nonwoven fabric as used for the liquid-permeable sheet 36. Here, the reinforcing member 135 and the liquid-permeable sheet 136 are bonded to each other through a hot-melt type adhesive applied to such an extent as not to interfere with liquid passage.

Between front and rear starting points 131, 132, the surface element 102 forms a three-dimensional structure 103, as shown in FIG. 4. As shown in FIG. 6, the three-dimensional structure 103 is hollow and the width between walls 133, 133 gradually increases from an apex 103a toward the napkin body 2 to provide protrusion apexes 103b, 103b, between which the width is brought to a maximum, at a level spaced upward from the skin-side surface of the napkin body 2 by 10 mm or more. Then, the width gradually decreases from the left and right protrusion apexes 103b, 103b to the skin-side surface of the napkin body 2. At its base, moreover, the three-dimensional structure 103 extends laterally to provide joining members 134, 134 throughout the length of the three-dimensional structure 103, and the joining members 134, 134 are bonded to and fixed on the skin-side surface of the napkin body 2 through a hot-melt type adhesive.

In the three-dimensional structure 103, the reinforcing member 135 is formed with compressed portions 137. The compressed portions 137 are formed in the walls 133, 133 to extend from the skin-side surface of the napkin body 2 to the apex 103a in a direction substantially perpendicular to the longitudinal direction. The compressed portions 137 are spaced in the longitudinal direction and extend parallel to each other.

In the three-dimensional structure 103, the front starting point 131 is located 10 to 20 mm forward of the vagina-facing reference line X1, while the rear starting point 132 is located slightly forward of the coccyx-facing reference line X3. Thus, the three-dimensional structure 103 can be brought into close contact with the wearer's body from the region posterior to the vaginal opening to the intergluteal cleft.

Forward of the front starting point 131, as shown in FIGS. 4 and 5, the surface element 102 is folded flat and substantially entirely fixed to the skin-side surface of the napkin body 2 to provide a front flattened portion 104. As also seen from FIG. 4, a rear flattened portion 105 is likewise formed rearward of the rear starting point 132.

In the sanitary napkin 101 according to the second embodiment, the protrusion apexes 103b, 103b are provided in the walls 133, 133 of the three-dimensional structure 103 and above them, the width of the three-dimensional structure 103 gradually decreases toward the apex 103a. When the sanitary napkin 101 is worn in the crotch, accordingly, the portion above the protrusion apexes 103b, 103b is allowed to come into close contact with the body's groove. With the protrusion apexes 103b, 103b, moreover, the three-dimensional structure 103 is allowed to be easily deformed toward the skin-side surface of the napkin body 2 by a pressure exerted on the apex 3a. This enables the three-dimensional structure 103, which is in close contact with the body's groove, to be freely deformed when the depth of the body's groove changes during sleep.

Since the three-dimensional structure 103 is designed to come into close contact with the labia at a location adjacent the front starting point 131, menstrual blood discharged from the vaginal opening can be immediately collected by the three-dimensional structure 103. In addition, since the front flattened portion 104 is designed to come into close contact with the anterior part of the vaginal opening, the degree of adhesion to the vaginal opening is improved in this part, so that menstrual blood can be collected by the reinforcing member 135 to effectively prevent lateral leakage of menstrual blood.

Figure 7:
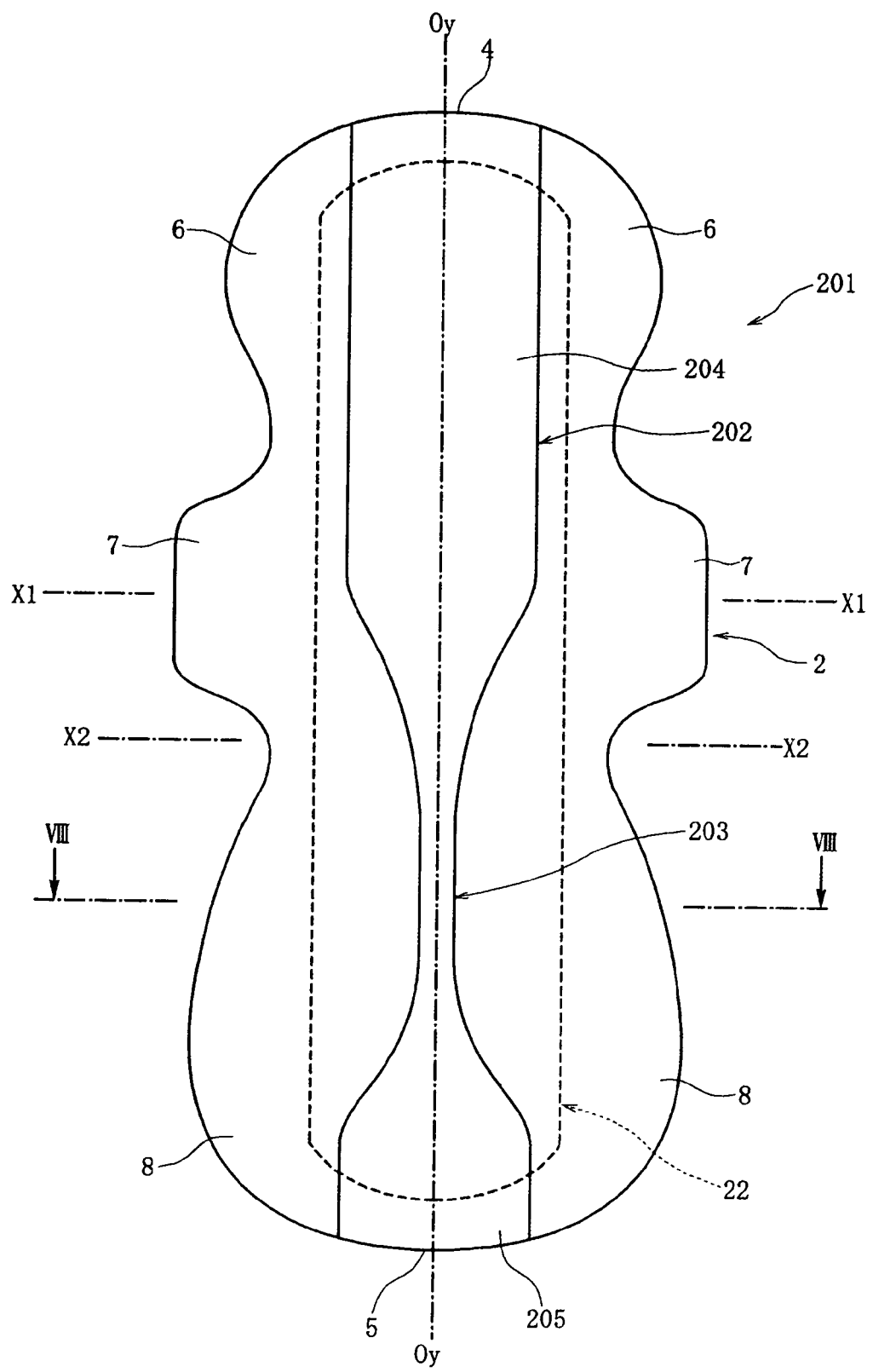
FIG. 7 is a plan view showing a sanitary napkin according to a third embodiment of the invention.
Figure 8:
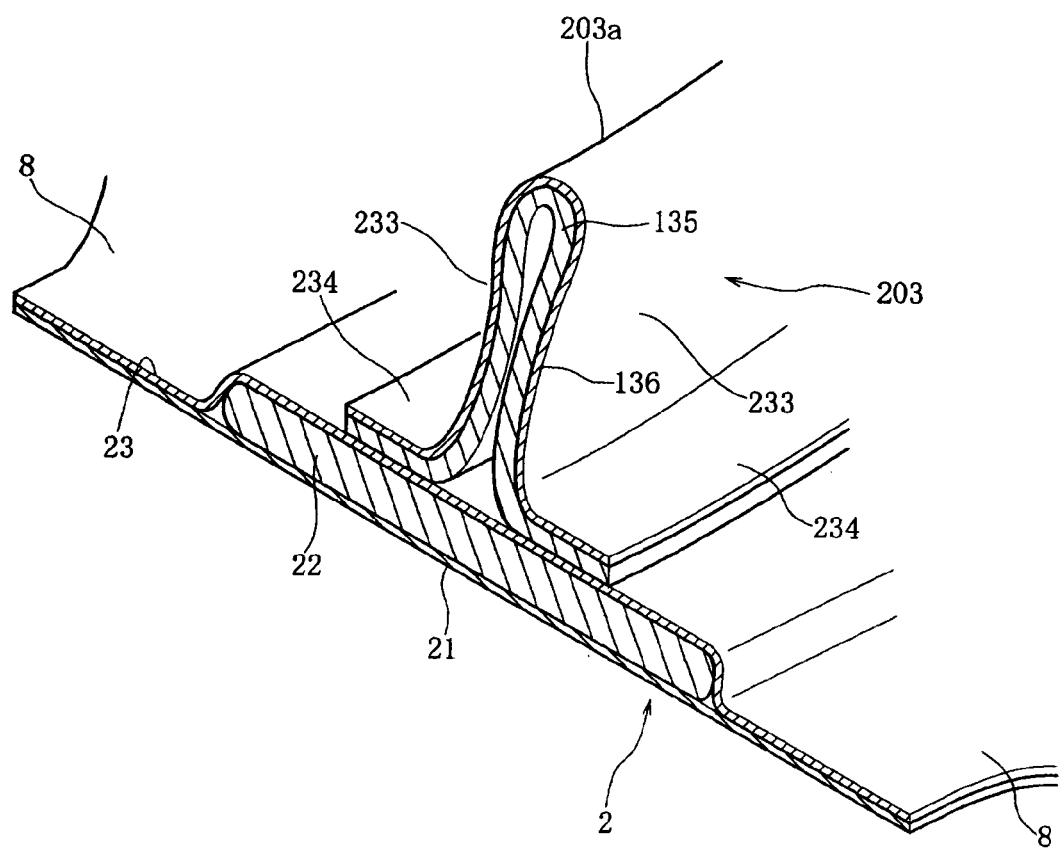
FIG. 8 is a transverse sectional view of the sanitary napkin of FIG. 7 taken along line VIII-VIII.

FIG. 7 is a plan view showing a sanitary napkin 201 according to a third embodiment of the present invention, and FIG. 8 is a sectional view of the sanitary napkin 201 of FIG. 7 taken along line VIII-VIII.

The napkin body 2 according to the third embodiment has the same construction as the napkin body of the first embodiment. In addition, a surface element 202 according to the third embodiment is composed of the reinforcing member 135 and the liquid-permeable sheet 136, like the surface element 102 according to the second embodiment. The surface element 202 forms a three-dimensional structure 203 and front and rear flattened portions 204, 205 located forward and rearward thereof, as shown in FIG. 7. The front and rear flattened portions 204, 205 are formed with the surface element 202 folded in the same manner as the front flattened portion 104 shown in FIG. 5.

In the sanitary napkin 210 according to the third embodiment, as shown in FIG. 8, the three-dimensional structure 203 has joining members 234, 234 at its base, which are bonded to the skin-side surface of the napkin body 2, and inner surfaces of walls 233, 233 are bonded to each other at a level spaced downward from an apex 203a of the three-dimensional structure 203.

As shown in FIG. 7, accordingly, the three-dimensional structure 203 is gradually narrowed in width rearwardly from adjacent the vagina-facing reference line X1 to have a minimum width in a portion which is intended to face the range from the anus (iv) to the location (vi) 50 mm posterior of the anus. Then, the width gradually increases rearwardly of the napkin. Since the three-dimensional structure 203 is narrowed in width in the portion intended to face the intergluteal cleft, this narrowed portion can easily make its way into the contact portion at the deepest part of the intergluteal cleft.

Figure 9A:
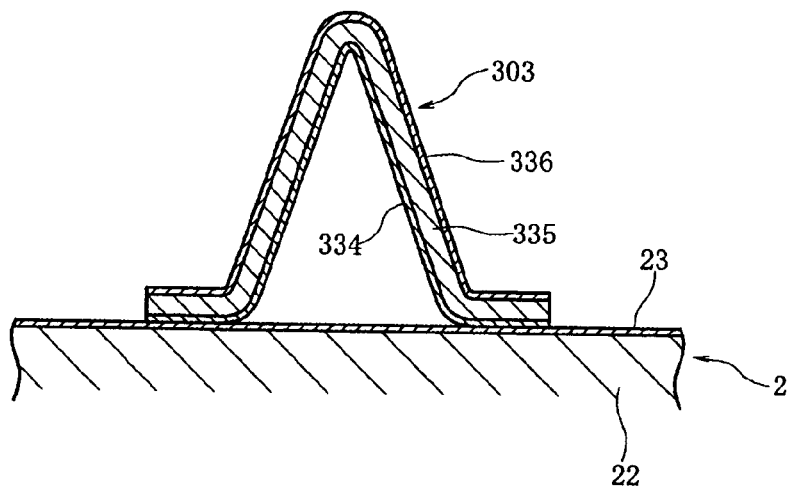
FIGS. 9(A), 9(B) and 9(C) are transverse sectional views showing three-dimensional structures according to different embodiments.
Figure 9B:
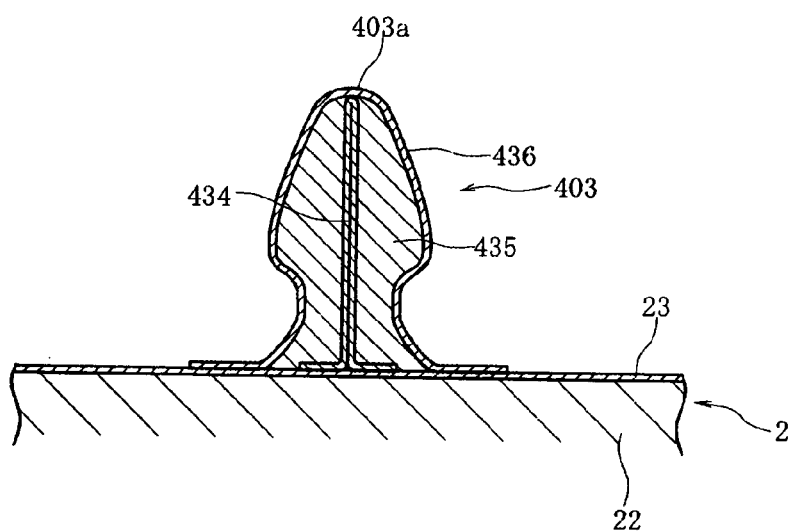
Figure 9C:
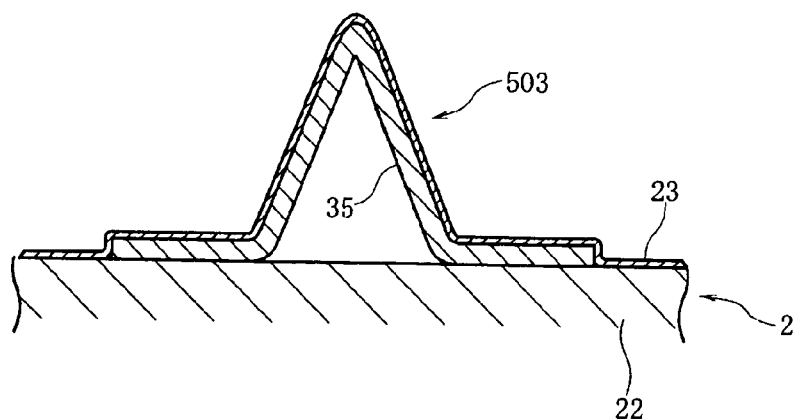

FIGS. 9(A), 9(B) and 9(C) are sectional views showing modifications of the three-dimensional structure mounted on the skin-side surface of the napkin body.

FIG. 9(A) shows a three-dimensional structure 303 in which a reinforcing member 334 is bonded to the inner surface of a liquid absorbent layer 335 which may be formed of an air-laid nonwoven fabric having the function of absorbing liquid, an air-laid nonwoven fabric only of pulp (air-laid pulp), a paper, or a spunlaced nonwoven fabric of rayon fibers. The reinforcing member 334 may be a paper, a urethane foam sheet, or a polyethylene foam sheet. On the other hand, the outer surface of the liquid absorbent layer 335 is covered with a liquid-permeable sheet 336.

FIG. 9(B) shows a three-dimensional structure 403 which is provided centrally with a reinforcing member 434 such as paper or polyurethane foam which is so flexible as to be easily buckled by a load exerted on an apex 403a, wherein a soft cushion layer 435 formed of a through-air bonded nonwoven fabric or the like is provided on both sides of the reinforcing member 434 and its outer surface is covered with a liquid-permeable sheet 436.

FIG. 9(C) shows a three-dimensional structure 503 in which the reinforcing member 35, which is not changed from that used in the first embodiment, is covered with the topsheet 23.

Here will be described preferred height H of the three-dimensional structure 3 and preferred stiffness of the three-dimensional structure 3.

As shown in FIG. 11, the body's groove is divided into the noncontact portion of the depth D1 where the opposing surfaces of the buttocks are separated from each other and the contact portion of the depth D2 where the opposing surfaces of the buttocks are in contact with each other. When measured in the standing position with the said female subject's legs closed, the depth D1 of the noncontact portion varied between about 10 and 25 mm, as shown in FIG. 12. Then, the depth D2 of the contact portion varied between 10 and 20 mm when measured in the standing position with her legs closed. Therefore, the total depth (D1+D2) of the body's groove in the standing position varies between 20 and 45 mm.

When measured in the supine position with the subject's legs closed, on the other hand, the depth D1 of the noncontact portion varied between about 5 and 20 mm, as shown in FIG. 12. Then, the depth D2 of the contact portion varied between about 10 and 15 mm, and therefore, the total depth (D1+D2) of the groove in the supine position varies between 15 and 35 mm.

The three-dimensional structure 3 is intended to come into contact with the body's groove in an upper portion above the level which is spaced about 10 mm from the skin-side surface of the napkin body. Accordingly, the maximum height $H_{max}$ of the three-dimensional structure 3 shown in FIG. 2 is preferably up to 60 mm and also preferably at least 25 mm.

Also measured were resistances caused by penetration into the deepest part of the body's groove of the subject.

For this measurement, used were measuring heads prepared by covering a rigid plastic having a length of 40 mm and a height of 30 mm with a through-air bonded nonwoven fabric. The used measuring heads were of four types: 1.03 mm, 5.15 mm, 10.3 mm and 15.45 mm in thickness. With the subject's legs closed in the standing position, the measuring head was inserted into the body's groove at a location midway between the location (iii) and the location (vi) shown in FIGS. 10 and 12 and then the load required for the tip of the measuring head to reach the deepest part of the contact portion was measured. The results are as follows:

| (Thickness) | 1.03 mm | 5.15 mm | 10.3 mm | 15.45 mm |
|---|---|---|---|---|
| (Load for Insertion) | 0.65 N | 4.36 N | 8.21 N | 12.8 N |
| (Equivalent) | 0.158 N | 0.212 N | 0.199 N | 0.207 N |

The equivalent is obtained by converting the load required to reach the deepest part of the body's groove to a load per unit area of the measuring head having a width of 1 mm and a length of 10 mm. From the above measurement, it is seen that the resistance from the wearer's body when reaching the deepest part of the body's groove is about 0.2 N per unit area having a width of 1 mm and a length of 10 mm.

Referring to FIG. 12, the depth D1 of the noncontact portion during sleep may be about 15 mm at a minimum within the range from the vaginal opening (ii) to the location (vii) 80 mm posterior of the anus. Here, the total depth (D1+D2) of the body's groove is up to about 45 mm in the standing position, as set forth above. Hence, when the three-dimensional structure 3 is pushed back by the skin in the supine position after having reached the deepest part of the body's groove in the standing position, the maximum height $H_{max}$ of the apex 3a of the three-dimensional structure 3 may be reduced at a ratio of $\{(45-15)/45\}\times100=66\%$.

Accordingly, if the reduction in height is equal to or less than 66% when a pressure of 0.2 N per unit area having a width of 1 mm and a length of 10 mm is applied to the apex 3a at the location where the three-dimensional structure 3 has the maximum height $H_{max}$ as shown in FIG. 2, the three-dimensional structure 3 can be kept in close contact with at least the noncontact portion in the most part of the body's groove even when the wearer alters her position from the standing position to the supine position.

Also measured was a maximum load which didn't make the subject unpleasant when the measuring head was inserted into the body's groove of the subject in the supine position with her legs closed, and the load was converted to a load per unit area having a width of 1 mm and a length of 10 mm in the same manner as described above.

| (Thickness) | 1.03 mm | 5.15 mm | 10.3 mm | 15.45 mm |
|---|---|---|---|---|
| (Maximum Load) | 1.213 N | 9.57 N | 12.39 N | 16.26 N |
| (Equivalent) | 0.303 N | 0.464 N | 0.300 N | 0.263 N |

From the above measurement, it is seen that the subject does not feel unpleasant if a force exerted by the three-dimensional structure 3 on the wearer's body is 0.3 N per unit area having a width of 1 mm and a length of 10 mm.

From FIG. 12, it is seen that the depth of the body's groove may be reduced approximately at a ratio of $\{(25-20)/25\}\times100=20\%$ when the wearer alters her position from the standing position to the supine position.

Accordingly, if the reduction in height at the apex is equal to or greater than 20% when a force of 0.3 N per unit area having a width of 1 mm and a length of 10 mm is applied to the apex at the location where the three-dimensional structure 3 has the maximum height $H_{max}$, the three-dimensional structure 3 does not give an unpleasant feeling to the wearer even when the depth of the body's groove varies during sleep, so that the three-dimensional structure 3 can be kept in close contact with the body's groove.

It should be noted that for the reinforcing member, at least one elastic member such as a rubber string may be provided in a tensioned state between the front and rear starting points 31, 32 for exerting an elastic contractive force to bring the front and rear starting points 31, 32 closer to each other. The napkin body 2 is curved by the elastic contractive force of the elastic member with the liquid-permeable sheet on the skin-side surface of the napkin body 2 being raised away from the skin-side surface to provide the three-dimensional structure 3. In this construction, the portion having the elastic member becomes the apex 3a of the three-dimensional structure 3 and the walls 33, 33 are formed of the liquid-permeable sheet.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the features set out in the appended claims.

What is claimed is:

1. An elongated sanitary napkin comprising:
    a napkin body containing a liquid absorbent layer for absorption and retention of liquid and having a vagina-facing region and an intergluteal cleft-facing region rearward of the vagina-facing region, wherein:
    a three-dimensional structure is provided in the intergluteal cleft-facing region to bulge from a skin-side surface of the napkin body with an apex spaced from the skin-side surface, wherein the three-dimensional structure is hollow along its entire length, and
    the three-dimensional structure has a liquid-permeable sheet which is exposed externally and a reinforcing member which is located beneath the liquid-permeable sheet, and
    the reinforcing member is enabled to be elastically deformed to reduce a height of the three-dimensional structure when a pressure toward the napkin body is exerted on the apex of the three-dimensional structure, wherein:
    the reinforcing member includes a fibrous layer forming walls of the three-dimensional structure, the walls having compressed portions that extend linearly upward from the skin-side surface of the napkin body to the apex of the three-dimensional structure, and
        wherein, the walls of the three-dimensional structure meet solely at the apex, and
        wherein the three-dimensional structure extends upward from the skin-side surface of the napkin body at different base points alone the longitudinal axis such that the width of the three-dimensional structure varies continuously along the longitudinal axis, and
        wherein the compressed portion of the walls extending linearly upwards are spaced at intervals in the longitudinal direction.

2. The sanitary napkin of claim 1, wherein the three-dimensional structure has front and rear starting points from which the three-dimensional structure starts to bulge from the skin-side surface of the napkin body, the three-dimensional structure having a maximum bulging height from the skin-side surface at a location midway between the front and rear starting points, the location where the bulging height is maximum being located on or rearward of an anus-facing region of the napkin body.

3. The sanitary napkin of claim 1, wherein when a pressure in a direction perpendicular to the skin-side surface of the napkin body is applied to the apex of the three-dimensional structure at the location where the three-dimensional structure has a maximum height and the pressure reaches 0.2 N per unit area of the apex having a width of 1 mm and a length of 10 mm, a reduction in height at the apex is equal to or less than 66%.

4. The sanitary napkin of claim 1, wherein when a pressure in a direction perpendicular to the skin-side surface of the napkin body is applied to the apex of the three-dimensional structure at the location where the three-dimensional structure has a maximum height and the pressure reaches 0.3 N per unit area of the apex having a width of 1 mm and a length of 10 mm, a reduction in height at the apex is equal to or greater than 20%.

5. The sanitary napkin of claim 1, wherein the fibrous layer has a function of absorbing liquid and is in close contact with the liquid-permeable sheet inside the three-dimensional structure.

6. The sanitary napkin of claim 1, wherein the three-dimensional structure is narrower in width in an intermediate portion than in front and rear portions.

7. The sanitary napkin of claim 1, wherein the three-dimensional structure is shaped to gradually decrease in width from a base adjacent to the skin-side surface toward the apex.

8. The sanitary napkin of claim 1, further comprising:
    one or more pressure-sensitive adhesive layers disposed on a backsheet of the napkin body and beneath one or more joining pieces of the three-dimensional structure, the one or more pressure-sensitive adhesive layers being provided for firmly fixing the napkin body to an undergarment of a wearer of the elongated sanitary napkin.

9. The sanitary napkin according to claim 1, wherein
    the three-dimensional structure has a width of 15 to 45 mm and an apex width of 1 to 5 mm, and
    the reinforcing member includes a fibrous layer forming opposing walls of the three-dimensional structure which extend in cross-section linearly upwardly to meet at the apex to define an angle θ between the opposing walls, wherein the angle θ has a value of 60 degrees or less.

10. The sanitary napkin of claim 9, wherein the three-dimensional structure has front and rear starting points from which the three-dimensional structure starts to bulge from the skin-side surface of the napkin body, the three-dimensional structure having a maximum bulging height from the skin-side surface at a location midway between the front and rear starting points, the location where the bulging height is maximum being located on or rearward of an anus-facing region of the napkin body.

11. The sanitary napkin of claim 9, wherein when a pressure in a direction perpendicular to the skin-side surface of the napkin body is applied to the apex of the three-dimensional structure at the location where the three-dimensional structure has a maximum height and the pressure reaches 0.2 N per unit area of the apex having a width of 1 mm and a length of 10 mm, a reduction in height at the apex is equal to or less than 66%.

12. The sanitary napkin of claim 9, wherein when a pressure in a direction perpendicular to the skin-side surface of the napkin body is applied to the apex of the three-dimensional structure at the location where the three-dimensional structure has a maximum height and the pressure reaches 0.3 N per unit area of the apex having a width of 1 mm and a length of 10 mm, a reduction in height at the apex is equal to or greater than 20%.

13. The sanitary napkin of claim 9, wherein the reinforcing member includes a fibrous layer which has a function of absorbing liquid and is in close contact with the liquid-permeable sheet inside the three-dimensional structure.

14. The sanitary napkin of claim 9, wherein the three-dimensional structure is narrower in width in an intermediate portion than in front and rear portions.

15. The sanitary napkin of claim 9, wherein the three-dimensional structure is shaped to gradually decrease in width from a base adjacent to the skin-side surface toward the apex.

16. The sanitary napkin of claim 9, further comprising:
    one or more pressure-sensitive adhesive layers disposed on a backsheet of the napkin body and beneath one or more joining pieces of the three-dimensional structure, the one or more pressure-sensitive adhesive layers being provided for firmly fixing the napkin body to an undergarment of a wearer of the elongated sanitary napkin.

* * * * *